United States Patent [19]
Voss

[11] Patent Number: 5,469,732
[45] Date of Patent: Nov. 28, 1995

[54] METHOD AND DEVICE FOR GAS ANALYSIS

[75] Inventor: Gunter Voss, Much, Germany

[73] Assignee: Auditec GmbH, Germany

[21] Appl. No.: 239,140

[22] Filed: May 6, 1994

[30] Foreign Application Priority Data

May 15, 1993 [DE] Germany ............... 43 16 196.0

[51] Int. Cl.⁶ .................................................. G01N 7/10
[52] U.S. Cl. .................. 73/31.04; 73/24.04; 73/29.01
[58] Field of Search ................. 73/24.01, 24.04, 73/29.01, 29.03, 31.04

[56] References Cited

U.S. PATENT DOCUMENTS

| | | | |
|---|---|---|---|
| 3,981,176 | 9/1976 | Jacobs | 73/24.01 |
| 4,051,372 | 9/1977 | Aine | 73/24.02 |
| 4,112,736 | 9/1978 | Wheldon et al. | 73/31.04 |
| 4,119,950 | 10/1978 | Redding | 73/24.01 |
| 4,555,932 | 12/1985 | Crosby, Jr. | 73/24.01 |
| 4,637,987 | 1/1987 | Minten et al. | 73/31.04 |
| 4,703,646 | 11/1987 | Müller et al. | 73/24.01 |
| 4,740,086 | 4/1988 | Oehler et al. | 356/432 |
| 5,076,094 | 12/1991 | Frye et al. | 73/24.01 |
| 5,101,656 | 4/1992 | Miller | 73/31.04 |
| 5,159,843 | 11/1992 | Shakkottai et al. | 73/24.01 |

*Primary Examiner*—Hezron E. Williams
*Assistant Examiner*—Eric S. McCall
*Attorney, Agent, or Firm*—Harris Beach & Wilcox

[57] ABSTRACT

Analyzing gas samples wherein the sample is passed into a measurement chamber via a molecular diffusion filter. The composition or pressure of the gas is changed with time as it moves through the filter and a pressure sensor within the measurement chamber is arranged to record pressure changes with respect to amplitude and time due to the difference in diffusion times of the gas components in the measured sample.

17 Claims, 2 Drawing Sheets

METHOD AND DEVICE FOR GAS ANALYSIS

BACKGROUND OF THE INVENTION

This invention relates to a method of analysis for gases and gas mixtures as well as instruments based on this method.

The instruments commonly used for gas analysis today operate with sensors which are in contact with the gas which is to be analyzed and which react more or less specifically to the components present in the gas. They usually supply electric signals from which one may conclude as to the partial pressure or the concentration of a type of gas which surrounds the sensor. In order to analyze several gases, either several sensors or highly complex measurement equipment such as mass spectrometers or spectroscopic instruments are required.

From EP 0,387,685 a method of gas analysis is known which is based on an acoustic modulation of the gas which is to be analyzed. In contrast to the method described in the following, pressure modulation is not used to utilize differing diffusion times; also the recording section of the analyzer is not a pressure sensor but a specific infra-red sensor.

From DE-GM 18 38 921 a method of gas analysis is known where the gas which is to be analyzed is linked via a molecular diffusion path to a measurement chamber in which the pressure variations are detected by means of a pressure sensor. The arising diffusion pressure is related to the concentration of a component in the gas.

However, several gases may give rise to the same diffusion pressure at suitable concentrations, a quantitative determination which is based on this method requires additional knowledge as to the composition of the gas; a general qualitative analysis is not possible.

The present invention is aimed at a qualitative and quantitative detection of the partial pressures of a gas mixture in connection with unspecific pressure sensors. Gas analyzers which are based on this configuration shall thus be much less complex and more rugged compared to conventional multi-component analyzers. For typical single component measurements such as in helium leak detection the sensitivity of these sensors should be comparable or superior to standard instruments.

This task is solved by a method having the features of claim 1 as well as a device having the features of claims 6 and 15. Extensions offering further advantages to this result from the sub-claims. Here the composition or the pressure of the gas which is to be analyzed is first modulated (periodic modulation is preferred). After flowing through a molecular separating device, the gas produces a varying total pressure in a measurement chamber, the phase of which is characteristic for each type of gas and where the amplitudes depend on the concentrations.

The method of measurement is based on the known fact that gases which differ in atomic or molecular weight behave differently in molecular flows or in diffusion processes (refer to Wutz, Adam, Walcher, "Theorie und Praxis der Vakuumtechnik", 5th Edition, Burnswick, Vieweg, 1992 p. 28–31 and 102–106). Simplifying one may say that lighter gases generally diffuse faster through diffusion paths (capillaries, sintered bodies, filter discs, porous filters and polymers among others) compared to heavier gases. In purely mechanical diffusion paths, such as sintered bodies or porous filters, for example, the diffusion speeds of two gases relate to each other approximately according to the inverse square roots of their respective molecular weights.

DESCRIPTION OF THE INVENTION

Figure 1:
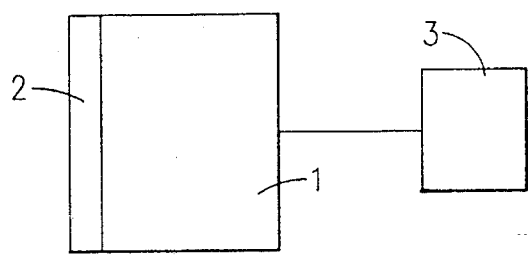
FIG. 1 shows schematically a minimum configuration to demonstrate the physical effect.

Turning now to the drawings wherein like numbers are used to identify like components, a simple arrangement which utilizes the above property for the purpose of measurement is shown in FIG. 1. Measurement chamber 1 is sealed with a fine porous filter disc 2 which is also used for common litering purposes. The pressure in measurement chamber 1 is measured with pressure sensor 3. To start with, let us consider the presence of the same gas, for example nitrogen, inside and outside of the measurement chamber. The system is at an equilibrium, i.e., the same pressure $p_0$ prevails inside and outside. Now, at the time $t_0$ the outside of the filter disc is brought into contact with a lighter gas, hydrogen, for example. Due to the concentration gradient, the process of diffusion will start immediately: hydrogen will penetrate the measurement chamber and nitrogen escapes. If the pores in the filter disc are sufficiently small, i.e., comparable to the mean free path of the gas molecules, the two diffusion processes will take place all different speeds. At first, more hydrogen will diffuse into the chamber than nitrogen will be capable of escaping; finally, the nitrogen concentrations will also equalize and the system again tends in the direction of the equilibrium pressure $p_0$ (for this refer to Wutz, Adam, Walcher, "Theorie und Praxis der Vakuumtechnik", 5th Edition, Brunswick, Vieweg, 1992, p. 28–31).

Figure 2:
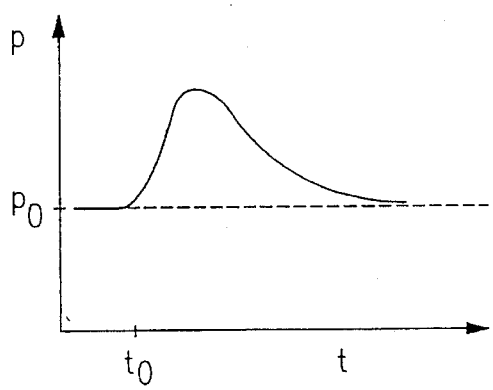
FIG. 2 shows the pressure versus time after replacing a gas of high molecular weight by a lighter gas.

Shown in FIG. 2 is the qualitative change in pressure p in the measurement chamber as a function of time t. From the theory of diffusion one may derive that the pressure change can be described by the superimposition of two exponential functions having different time constants:

$$p(t)=A\times exp(-at)+B\times[1-exp(-bt)]$$

where p is the pressure in the chamber, t is the time and a and b are the time constants for both diffusion directions. A and B are coefficients which depend on the initial conditions.

Figure 3:
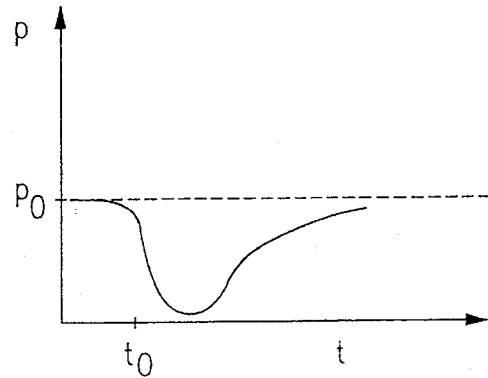
FIG. 3 shows the pressure versus time after replacing a gas of low molecular weight by a heavier one.

When removing the hydrogen at time $t_1$ replacing it by nitrogen once more, the process will be reversed: at first the pressure drops because the hydrogen escapes much faster out of the chamber compared to the entering nitrogen and then the system will tend to its equilibrium pressure once more. This pressure change is shown in FIG. 3.

If the measurement gas components have a higher molecular weight compared to the gas which was present in the system at the beginning, then a pressure reduction will occur initially, because this gas can only enter the measurement chamber at a slower rate compared to the rate of the gas escaping from the chamber. Equally, one expects a pressure rise after removing this gas.

As long as the system pressure does not exceed several bar, the processes described will be highly linear, i.e., the obtained pressure increases and pressure reductions will be strictly proportional to the concentrations of the gas components which are to be measured.

Figure 4:
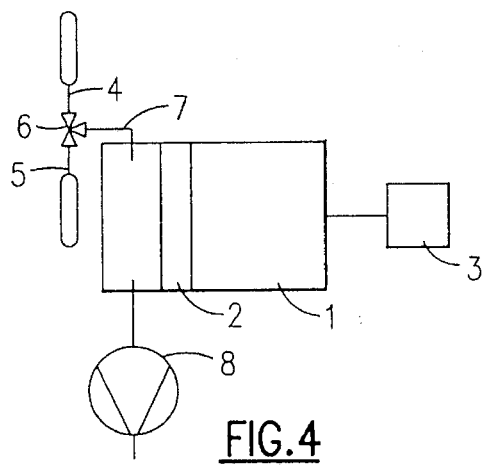
FIG. 4 shows a minimum configuration to use the effect periodically.

The described effect is of particular advantage when the measurement gas is periodically applied to, and removed from the filter disc. For this, as shown in FIG. 4, for example, a gas flow composed of the measurement gas 4 and a reference gas 5 (air, for example) are each applied to a valve 6, which periodically switches between the two gas flows. The resulting gas flow 7 alternatingly carries the reference gas and the measurement gas and this flow is directed past the filter disc with the aid of the pump 8.

Figure 5:
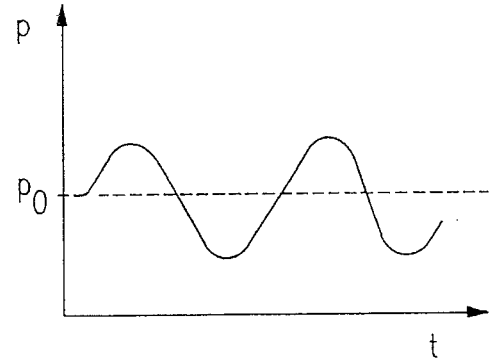
FIG. 5 shows the pressure versus time using the set-up in FIG. 4.

According to the processes described above, the pressure sensor 3 now registers a signal which periodically changes about the equilibrium pressure as long as the measurement gas contains a component which differs in molecular weight from the reference gas components. This effect is shown graphically in FIG. 5.

Figure 6:
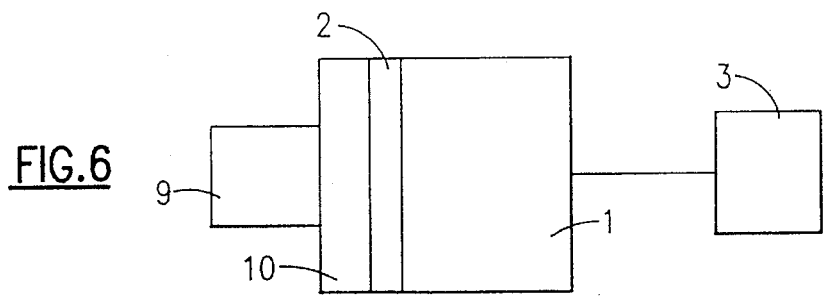
FIG. 6 is a variant of FIG. 4 by replacing the valve by an acoustic modulator.

The pressure changes will always occur in the measurement chamber when the concentration gradient across the diffusion path (in this example a filter disc) changes. Instead of periodically switching between two gas flows it is for this reason also possible to periodically modulate the pressure in the measurement gas. A simple means of modulating the pressure is shown in the example of FIG. 6. An acoustic signal source 9 (loudspeaker, for example) causes acoustic vibrations of a suitable frequency in the volume 10 in front of the filter disc. When the gas, which is to be analyzed flows through the volume 10 or fills it, the effect as described above will also occur.

When selecting a suitable modulation frequency, it is possible to use a micro,phone as the pressure sensor. Particularly small low-cost capacitor or electronic microphones as used in ordinary audio equipment deliver excellent results.

Figure 7:
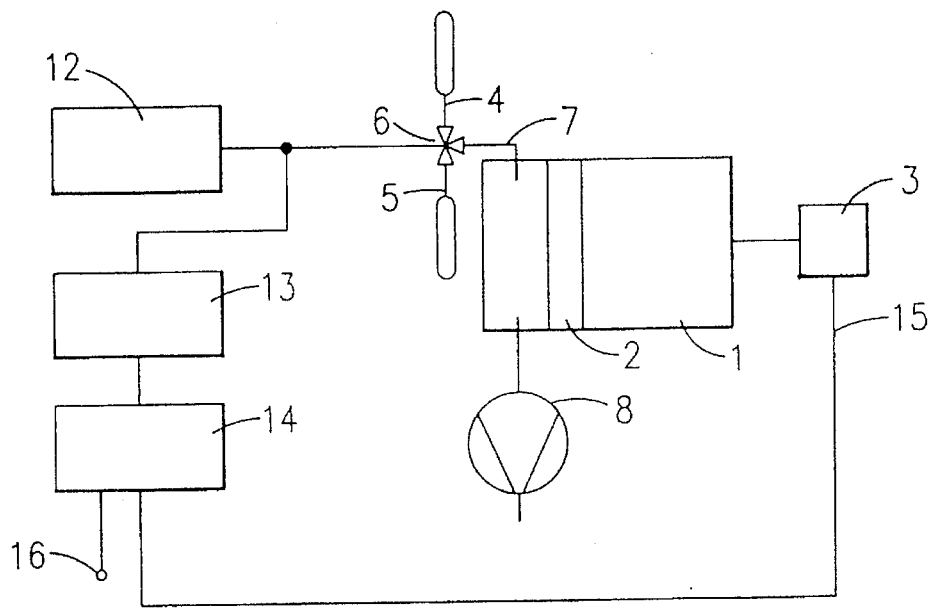
FIG. 7 is the apparatus for gas analysis of the present invention.

The capabilities of this method are decisively expanded when the AC signal obtained from the pressure sensor is subjected to phase-sensitive rectification. As is commonly known, the phase sensitive rectifier which is also called synchronous rectifier or lock-in amplifier considerably improves the signal to noise ratio (see Tietze, Schenk, "Halbleiterschaltungstechnik" 9th Edition, Berlin, Springer, 1991 p. 880–885). Thus interfering components in the pressure can be suppressed very effectively, especially when using microphones as pressure sensors. An example of apparatus for carrying out this process is shown in FIG. 7. The gas modulator (valve 6, for example or the acoustic sound source 9 as detailed in the examples above) is run at the frequency of the voltage generator 12. The same signal from the voltage generator is used to control the synchronous rectifier 14 after suitable phase correction 13. The AC signal which is available at the output of the pressure sensor 15 is thus converted into a DC voltage at output 16.

A different property of the phase-sensitive rectifier is its capability to fully neutralize synchronous signals having a certain phase relationship, i.e., having a phase of 90° with respect to the reference signal. By suitable selection of the size of the pores in the filter, plate thickness, volume of the measurement chamber and the modulation frequency in particular, the time constants of the described gas analyzers can be set up in such a way that exactly this phase relationship of 90° will occur between the signals supplied by the two components in the measurement gas. Thus, the signal from one of two components can be suppressed completely.

When alternatingly running the system with different modulation frequencies which are adapted to this property, it is then possible to fully analyze a gas mixture.

Figure 8:
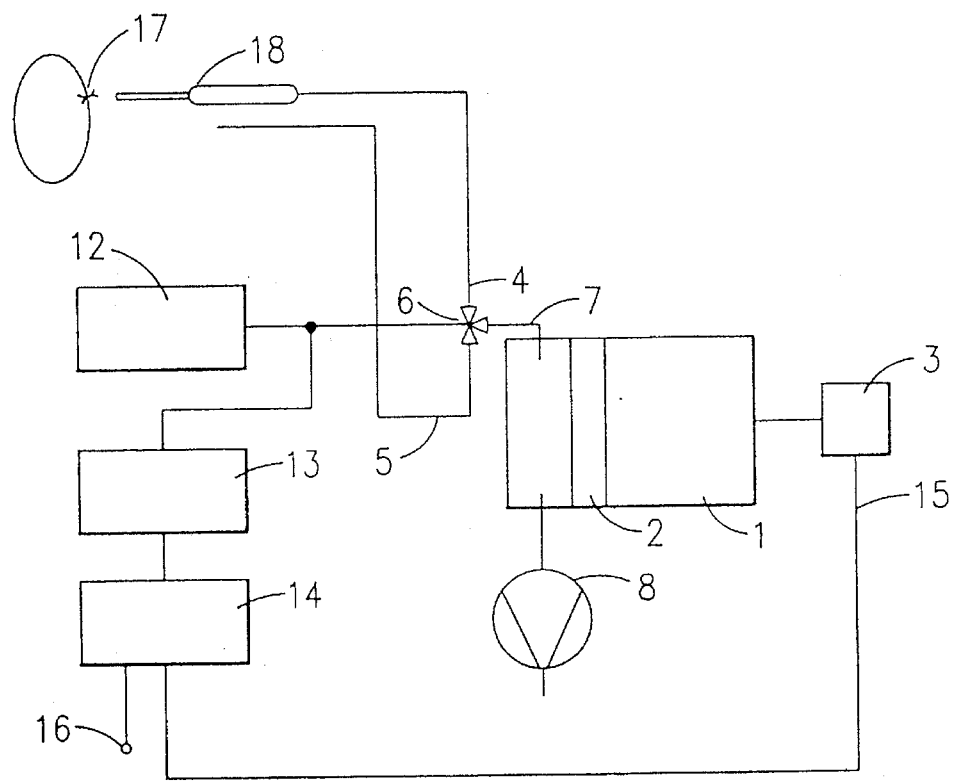
FIG. 8 is the set-up of FIG. 7 completed with a sniffer probe to get a sniffer leak detector.

The method is most powerful when wanting to detect low concentrations of a very light gas such as helium, for example, in a gas of a higher molecular weight such as air, for example. This is exactly the task of a helium leak detector. In helium leak detection, the helium test gas which enters through leaks is detected by gas analyzers (for this refer to Wutz, Adam, Walcher, "Theorie und Praxis der Vakuumtechnik", 5th Edition, Brunswick, Vieweg, 1992, p. 482–490); company publication from Leybold AG, "Grundlagen der Vakuumtechnik Berechnungen und Tabellen", Cologne, 1987, p. 63–68; Jansen, W., "Grundlagen der Dichtheltsprufung mit Hilfe yon Testgasen", in Vakuum Technik, Vol. 29, 1980, No. 4, p. 105–113). An example of a sniffer leak detector is shown in FIG. 8. Helium which is escaping through a leak 17 is applied via a sniffer tip 18 to a gas analyzer which operates with modulation valve 6 according to the method described above. The reference gas flow 5 is preferably sampled some centimeters away from the tip of the sniffer. This arrangement offers the advantage that helium from the ambient air enters into the analyzer through the measurement gas channel and also through the reference gas channel. Because this method only responds to differences between the channels, any helium which is enriched in the ambient air (helium background) will not contribute to the measurement signal. In particular, the natural helium content of the atmospheric air of about 5 ppm will now no longer have a restricting influence on the detection limit of the method of sniffer leak detection. In this arrangment the analyzer acts as a gradient detector for gas concentrations.

This method may also be utilized for the purpose of vacuum leak detection. In vacuum leak detection, the test object is evacuated and the test gas, normally helium, is applied from the outside. The test gas which enters through leaks is detected by means of gas analysis. Powerful standard instruments usually employ mass spectrometers for this.

The new method described here is, as opposed to instruments which are based on mass spectrometers, not dependent on the high vacuum. Thus, it will be sufficient to evacuate the test object to a low pressure and to apply a sample of the gas from the test object to the analyzer. This simplifies the required pump system and reduces the time required until the leak test can be run.

While this invention has been explained with reference to the structure disclosed herein, it is not confined to the details set forth and this invention is intended to cover any modifications and changes as may come within the scope of the following claims:

What is claimed is:

1. Method of analysis of gasses and gas mixtures where a gas which is to be analyzed is linked via a molecular diffusion path to a measurement chamber in which a pressure sensor registers pressure changes, wherein the pressure of gas (1) is modulated and wherein the pressure sensor (3) registers pressure changes according to their amplitude and time, which arise due to the different diffusion times of different gas components.

2. Method according to claim 1 wherein the modulation of the gas which is to be measured is produced by alternate pumping with a reference gas.

3. Method according to claim 1 wherein the modulation is produced through acoustic vibrations as pressure modulation.

4. Method according to claim 1 wherein the measurement gas is modulated periodically.

5. Method according to claim 1 wherein the pressure sensor supplies a signal which is subjected to phase-sensitive rectification.

6. Device for analysis of gases and gas mixtures with a gas supply system (7,8,10), through which a gas which is to be analyzed (4) is connected via a molecular diffusion path (2) to the gas supply system (7,10) and where a pressure sensor is able to record the pressure changes in a measurement chamber (1), wherein the device is equipped with a gas modulator (6,12,9) through which the gas which is to be analyzed (4) can be modulated in time as to its composition.

7. Device according to claim 6 wherein the diffusion path (2) is a porous filter.

8. Device according to claim 6 wherein the diffusion path (2) is a polymer foil.

9. Device according to claim 6 wherein the diffusion path is a mechanical channel.

10. Device according to claim 6 wherein the pressure sensor (3) is a total pressure sensor, the sensing properties of which do not depend on the type of gas.

11. Device according to claim 6 wherein the pressure sensor (3) is a thermal conductivity manometer.

12. Device according to claim 6 wherein the pressure sensor (3) is a gas friction manometer.

13. Device according to claim 6 wherein the pressure sensor is a microphone.

14. Device according to claim 6 wherein a signal (15) which is supplied by the pressure sensor (3) is subjected to phase-sensitive rectification by a rectifier device (13,14).

15. Leak detection device for leak tests with an analyzer with which a test gas, can be detected, wherein the analyzer is a device according to claim 6.

16. Method of analysis of gasses and gas mixtures where a gas which is to be analyzed is linked via a molecular diffusion path to a measurement chamber in which a pressure sensor registers pressure changes, wherein the composition of gas (1) is modulated and wherein the pressure sensor (3) registers pressure changes according to their amplitude and time, which arise due to the different diffusion times of different gas components.

17. Device for analysis of gases and gas mixtures with a gas supply system (7,8,10), through which a gas which is to be analyzed (4) is connected via a molecular diffusion path (2) to the gas supply system (7,10) and where a pressure sensor is able to record the pressure changes in a measurement chamber (1), wherein the device is equipped with a gas modulator (6,12,9) through which the gas which is to be analyzed (4) can be modulated in time as to its pressure.

* * * * *